United States Patent [19]

Jordan et al.

[11] Patent Number: 5,746,594
[45] Date of Patent: May 5, 1998

[54] ORTHODONTIC APPLIANCE WITH ASYMMETRIC BONDING STRUCTURE

[75] Inventors: Russell A. Jordan, Rancho Cucamonga; James D. Hansen, Duarte, both of Calif.

[73] Assignee: Minnesota Mining & Manufacturing Co., St. Paul, Minn.

[21] Appl. No.: 611,120

[22] Filed: Mar. 5, 1996

[51] Int. Cl.$^6$ .................................... A61C 3/00
[52] U.S. Cl. .................................... 433/9
[58] Field of Search .................... 433/8, 9, 4, 180

[56] References Cited

U.S. PATENT DOCUMENTS

| | | | |
|---|---|---|---|
| D. 290,040 | 5/1987 | Kelly | D24/16 |
| D. 340,523 | 10/1993 | Barngrover | D24/180 |
| 3,765,091 | 10/1973 | Northcutt | 433/9 |
| 3,932,940 | 1/1976 | Andren | |
| 4,094,068 | 6/1978 | Schinhammer | |
| 4,243,386 | 1/1981 | Kawaguchi | 433/9 |
| 4,322,206 | 3/1982 | Reynolds | 433/9 |
| 4,460,336 | 7/1984 | Smith et al. | 433/9 |
| 4,553,932 | 11/1985 | Armstrong et al. | 433/4 |
| 4,604,057 | 8/1986 | Viglietti | 433/9 |
| 4,626,209 | 12/1986 | Tsai et al. | 433/9 |
| 4,673,354 | 6/1987 | Culler | 433/217.1 |
| 4,752,221 | 6/1988 | Hanson et al. | 433/9 |
| 4,842,513 | 6/1989 | Haarmann | 433/9 |
| 4,936,773 | 6/1990 | Kawaguchi | 433/9 |
| 4,948,366 | 8/1990 | Horn et al. | 433/9 |
| 5,066,225 | 11/1991 | Forbes Jones et al. | 433/8 |
| 5,071,344 | 12/1991 | Wong et al. | 433/8 |
| 5,095,602 | 3/1992 | Recher et al. | 29/160.6 |
| 5,098,288 | 3/1992 | Kesling | 433/9 |
| 5,108,285 | 4/1992 | Tuneberg | 433/9 |
| 5,158,452 | 10/1992 | Franseen et al. | 433/9 |
| 5,267,854 | 12/1993 | Schmitt | 433/8 |
| 5,269,680 | 12/1993 | Kawaguchi | 433/9 |
| 5,295,823 | 3/1994 | Farzin-Nia | 433/9 |
| 5,350,059 | 9/1994 | Chester et al. | 206/63.5 |
| 5,354,199 | 10/1994 | Jacobs et al. | 433/9 |
| 5,362,232 | 11/1994 | Franseen et al. | 433/9 |
| 5,366,372 | 11/1994 | Hansen et al. | 433/4 |
| 5,380,196 | 1/1995 | Kelly et al. | 433/8 |
| 5,393,486 | 2/1995 | Eckert et al. | 419/66 |
| 5,395,237 | 3/1995 | Pospisil et al. | 433/8 |
| 5,429,229 | 7/1995 | Chester et al. | 206/63.5 |
| 5,435,720 | 7/1995 | Riebschleger | 433/9 |
| 5,438,379 | 8/1995 | Hansen | 433/8 |
| 5,441,408 | 8/1995 | Moschik | 433/8 |
| 5,445,408 | 8/1995 | Adam et al. | 264/16 |

*Primary Examiner*—Ralph Lewis
*Attorney, Agent, or Firm*—James D. Christoff

[57] ABSTRACT

An orthodontic appliance such as a bracket has bonding structure that provides a greater bond strength to the tooth in regions beneath an occlusal edge portion of the base in comparison to regions beneath at least one of a mesial edge portion, distal edge portion and occlusal edge portion of the base. The weaker bond strengths beneath the mesial edge portion, the distal edge portion and/or the gingival edge portion facilitate removal of the appliance by the orthodontist when desired. The higher bond strength beneath the occlusal edge portion is sufficient to securely retain the appliance on the tooth and safely resist the forces normally encountered during orthodontic treatment.

27 Claims, 3 Drawing Sheets

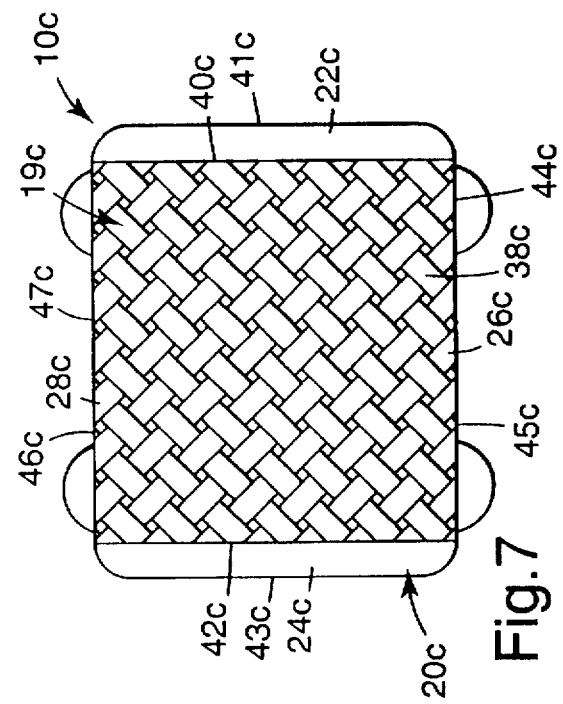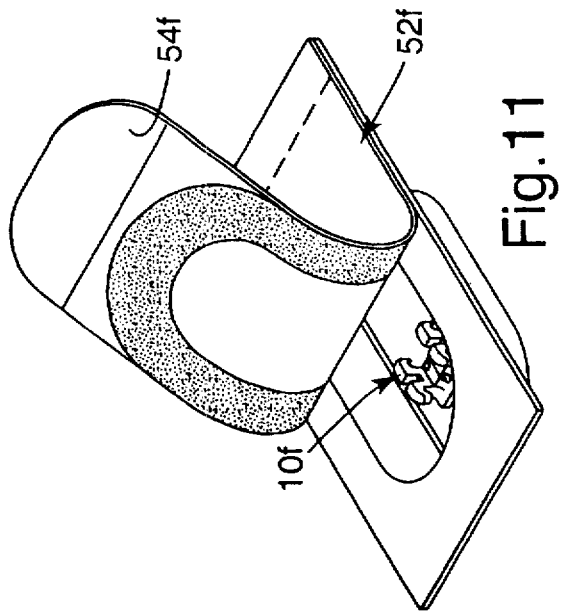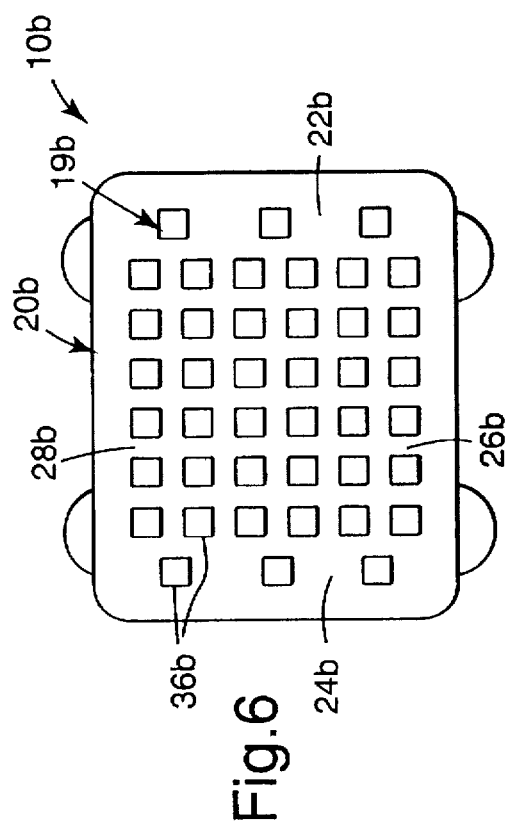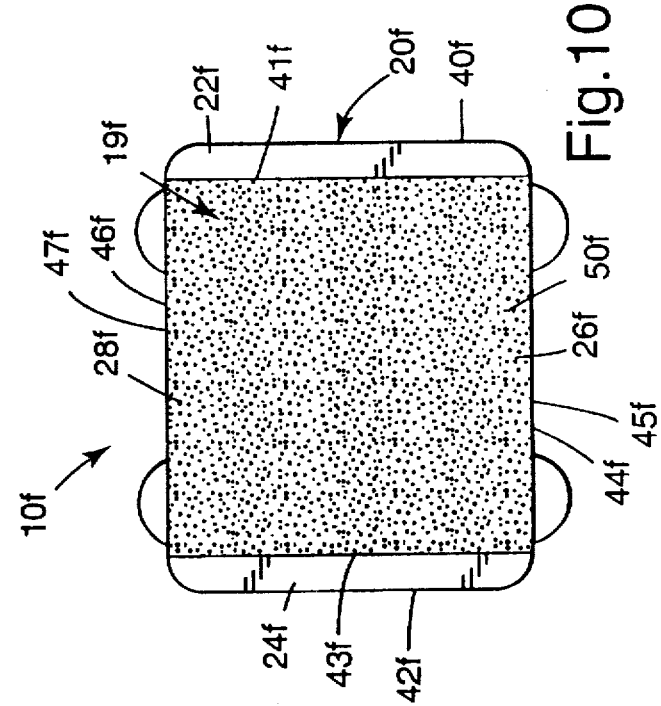

ORTHODONTIC APPLIANCE WITH ASYMMETRIC BONDING STRUCTURE

BACKGROUND OF THE INVENTION

1. Field of the Invention

This invention relates to an appliance that is used in orthodontic treatment and that has bonding structure adapted for directly affixing the appliance to a surface of the patient's tooth.

2. Description of the Related Art

Orthodontic treatment typically involves moving maloccluded teeth to orthodontically correct positions for improved occlusion and aesthetic appearance. During treatment, tiny, slotted appliances are affixed to the patient's teeth and an archwire is placed in the slot of each appliance. The archwire serves as a track to guide movement of the teeth to positions as selected by the orthodontist.

Orthodontic brackets are examples of appliances that are commonly affixed to the patient's anterior, cuspid and bicuspid teeth. Orthodontic brackets typically include a slot with an open side for insertion of the archwire, and one or more tiewings for connection to a ligating wire or elastic O-ring that is used to secure the archwire in the slot of the bracket. Examples of orthodontic brackets are described in U.S. Pat. Nos. 5,445,770, 5,395,237 and 5,380,196.

Buccal tubes are orthodontic appliances that are adapted for connection to the patient's molar teeth. Buccal tubes also have a slot for receiving an archwire, but the slot is often closed along its sides and open only at its ends, similar to an enclosed tubular passage. The slots of buccal tubes as well as the slots of brackets may have either a round, rectangular or square configuration when taken in reference planes perpendicular to the length of the slot.

In the past, orthodontic brackets and buccal tubes were often welded to bands that encircled the teeth. While the bands provide a means for securely connecting brackets and buccal tubes to the chosen teeth, the steps of selecting correctly fitting bands, welding of the bracket or buccal tube to each band and installation of the bands are somewhat time consuming and represent an additional expense. In addition, bands present a noticeable, metallic appearance that often serves as an embarrassment to the patient.

In recent years, increased usage has been made of orthodontic appliances and particularly orthodontic brackets that are directly bonded to the surface of teeth. The increased popularity of directly bonded brackets is due, in part, to the development of new adhesives which secure the base of each bracket to the tooth enamel with sufficient force to resist debonding as treatment progresses. Orthodontic brackets that are directly bonded to the teeth are less noticeable and hence considered more aesthetic than brackets that are welded to metallic bands.

A significant amount of attention has been directed to the bonding structure that is located on the base of directly bonded brackets. The bonding structure serves to reduce the likelihood of spontaneous debonding of the appliance from the tooth during orthodontic treatment. In some instances, the bracket may debond due to forces intentionally placed on the bracket by the orthodontist when attempting to move the underlying tooth to a desired position. For example, the orthodontist may bend or twist the archwire, or may connect a spring or elastic member to the bracket in order to move the associated tooth in a certain direction. In other instances, the bracket may debond due to the forces of mastication, such as when the patient bites into a relatively hard food object.

Brackets that spontaneously debond from the tooth during orthodontic treatment represent a nuisance that is best avoided. If, for example, a bracket debonds during treatment, the patient should return to the orthodontist, and the orthodontist will often remove the archwire, clean and prepare the tooth, bond a new bracket to the tooth and then re-engage the archwire in order to resume treatment. Such procedure is time consuming for both the patient as well as the orthodontist.

As a consequence, many manufacturers of orthodontic appliances have attempted to increase the bond strength of brackets directly bonded to teeth by modifying the adhesive or by modifying the base of the bracket that contacts the adhesive. The bases of some brackets, for example, are provided with a roughened or scribed surface that presents an increased area for contact with the adhesive. Roughened surfaces may be provided by sandblasting the base or by attaching grit or other particles to the base. Examples of such brackets are described in U.S. Pat. Nos. 4,626,209 and 4,243,386.

Some orthodontic brackets have a base with small undercut regions that contact the adhesive as the bracket base is embedded in the adhesive. Once the adhesive has hardened, the adhesive is mechanically interlocked to the undercuts of the base such that retention of the bracket on the tooth is improved. Examples of brackets having a base provided with undercut areas that may be formed in a machining operation are described in U.S. Design Pat. No. 290,040. Examples of brackets having bases with pegs or tabs presenting undercut areas are described in U.S. Design Pat. No. 340,523 and U.S. Pat. No. 5,393,486.

The base of some metal brackets are provided with a wire mesh pad that resembles a tiny screen. As the base of such brackets is embedded in the adhesive, the adhesive flows into the openings of the mesh pad and into areas between the mesh pad and the appliance body. The mesh pad provides undercut areas that enable the adhesive to mechanically interlock with the bracket once the adhesive has hardened.

In general, efforts by manufacturers to increase bond strength of brackets to the teeth have not unduly hindered removal of metal brackets when no longer needed. Metal brackets are often debonded by using a device such as is shown in U.S. Pat. No. 4,553,932, which exerts a pulling force on one side of the bracket and tends to bend and peel the base of the bracket away from the tooth surface. The peeling motion causes a crack to be propagated in the adhesive. The adhesive is often brittle and the bracket can be lifted from the tooth as soon as the crack has propagated through the adhesive.

However, orthodontic brackets that are made of relatively rigid material such as ceramic cannot be debonded from the teeth by a peeling motion because the ceramic material does not bend to any significant degree. Instead, such brackets are often debonded by prying or lifting one side of the bracket away from the tooth until a crack has propagated through the adhesive. In general, a substantially higher degree of force is required to debond a ceramic bracket than a metal bracket because the crack in the adhesive beneath the ceramic bracket must propagate through the adhesive essentially instantaneously, while the crack in the adhesive beneath the metal brackets need only propagate as fast as the peeling motion is carried out.

U.S. Pat. Nos. 5,366,372 and 5,439,379 describe improved ceramic brackets having mesial and distal sections that are debonded from the tooth by pivoting the sections toward each other about a central reference axis that extends in an occlusal-gingival direction. If desired, a pair of pliers or other tool may be used to squeeze and pivot the mesial and distal sections of the bracket together. The pivotal motion is believed to concentrate debonding stresses along outer, mesial and distal edges of the bracket base such that less stress is needed than the stresses needed, for example, to debond the bracket by pulling the bracket perpendicularly away from the tooth surface. The reduced stress to debond the bracket is a particular advantage if the underlying tooth structure is weak or has been damaged.

While the ceramic brackets described in U.S. Pat. Nos. 5,366,372 and 5,439,379 represent a significant advance in the art, there still remains a need for improved bonding structure for orthodontic appliances that facilitates removal of the appliance when desired. Preferably, such a bonding structure would be useful not only for appliances made of relatively rigid materials such as ceramics and certain plastics, but also for metallic appliances, especially if adhesives having higher bond strengths are developed and commercialized in the future.

SUMMARY OF THE INVENTION

The present invention is directed toward an improved bonding structure for orthodontic appliances that presents a relatively high resistance to debonding under the influence of forces exerted in a gingival direction (i.e., in a direction toward the patient's gingiva or gums), but can be readily debonded when desired when subjected to forces from other directions. As an example, the bracket may exhibit lower bond strength when subjected to a force in a mesial direction (i.e., in a direction toward the center of the patient's dental arch), in a distal direction (i.e., in a direction away from the center of the patient's arch), or in an occlusal direction (i.e., in a direction toward the tips of the patient's teeth). The appliance remains securely affixed to the tooth during the normal course of treatment, but can be readily debonded and removed when desired.

More particularly, an orthodontic appliance according to one aspect of the invention comprises a body having wall sections defining a slot for receiving an archwire, and bonding structure connected to the body for bonding the body to a tooth. The bonding structure includes an imperforate base having a mesial edge portion, a distal edge portion, a gingival edge portion and an occlusal edge portion. The bonding structure includes first means for bonding the mesial edge portion to a tooth with a first bond strength value, second means for bonding the distal edge portion to the tooth with a second bond strength value, third means for bonding the gingival edge portion to the tooth with a third bond strength value and fourth means for bonding the occlusal edge portion to the tooth with a fourth bond strength value. At least one of the first bond strength value, the second bond strength value and the third bond strength value is less than the fourth bond strength value.

Another aspect of the invention relates to an orthodontic appliance that comprises a body having wall sections defining a slot for receiving an archwire, and bonding structure connected to the body for bonding the body to a tooth. The bonding structure includes a base having a mesial edge portion, a distal edge portion, a gingival edge portion and an occlusal edge portion. The bonding structure also includes projections connected to the base and extending outwardly away from the body. Each of the projections has a certain surface area. The total surface area of any projections connected to one of the mesial edge portion, the distal edge portion and the gingival edge portion is less than the total surface area of any projections connected to the occlusal edge portion.

The invention is also directed toward an orthodontic appliance that comprises a body having wall sections defining a slot for receiving an archwire, and bonding structure connected to the body for bonding the body to a tooth. The bonding structure includes a base having a mesial edge portion, a distal edge portion, a gingival edge portion and an occlusal edge portion. The bonding structure includes a number of particles connected to the base. A greater quantity of particles are connected to the occlusal edge portion than are connected to at least one of the mesial edge portion, the distal edge portion and the gingival edge portion.

Another aspect of the invention concerns an orthodontic appliance that comprises a body having wall sections defining a slot for receiving an archwire, and bonding structure connected to the body for bonding the body to a tooth. The bonding structure includes a base having a mesial edge portion, a distal edge portion, a gingival edge portion and an occlusal edge portion each having a certain area. The bonding structure also includes a material covering at least part of the base for enhancing the bond strength of an orthodontic adhesive to the base. The material covers a larger percentage of the area of the occlusal edge portion than covers any percentage of the area of at least one of the mesial edge portion, the distal edge portion and the gingival edge portion.

The invention also relates to an orthodontic appliance comprising a body having wall sections defining a slot for receiving an archwire, and bonding structure connected to the body for bonding the body to a tooth. The bonding structure includes a base and a mesh pad connected to the base. The base and the mesh pad each have a mesial edge, a distal edge, a gingival edge and an occlusal edge. The mesial edge of the mesh pad is located a first distance from the mesial edge of the base, the distal edge of the mesh pad is located a second distance from the distal edge of the base, the gingival edge of the mesh pad is located a third distance from the gingival edge of the base and the occlusal edge of the mesh pad is located a fourth distance from the occlusal edge of the base. The fourth distance is less than at least one of the first, the second and the third distances.

Another embodiment of the invention concerns a packaged orthodontic article that comprises a container and an orthodontic appliance removably received in the container. The appliance includes a body having wall sections defining a slot for receiving an archwire and bonding structure connected to the body for bonding the body to a tooth. The bonding structure includes a base and a quantity of adhesive connected to the base. The base and the adhesive each have a mesial edge, a distal edge, a gingival edge and an occlusal edge. The mesial edge of the adhesive is located a first distance from the mesial edge of the base, the distal edge of the adhesive is located a second distance from the distal edge of the base, the gingival edge of the adhesive is located a third distance from the gingival edge of the base and the occlusal edge of the adhesive is located a fourth distance from the occlusal edge of the base. The fourth distance is less than at least one of the first, the second and the third distances.

Further details of these and other aspects of the invention are set out below in the detailed description of the preferred embodiments as well as in the accompanying drawings.

BRIEF DESCRIPTION OF THE DRAWINGS

FIG. 6 is a view somewhat similar to FIG. 4 but according to another embodiment of the invention;

FIG. 7 is a view somewhat similar to FIG. 4 in accordance with still another embodiment of the invention;

FIG. 10 is a view somewhat similar to FIG. 4 in accordance with another embodiment of the invention; and FIG. 11 is an illustration of the appliance depicted in FIG. 10 wherein the appliance is received in a container.

DETAILED DESCRIPTION OF THE PREFERRED EMBODIMENTS

Figure 1:
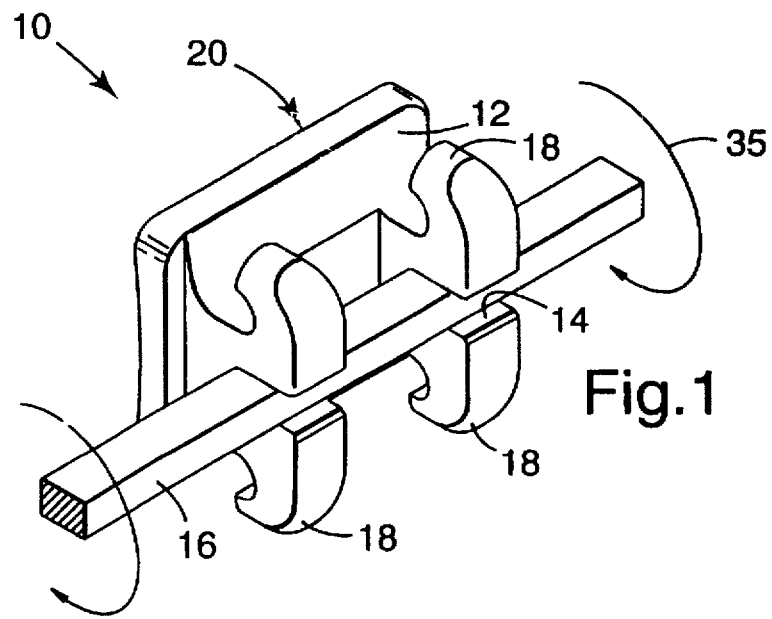
FIG. 1 is a isometric view of an orthodontic appliance constructed in accordance with one embodiment of the present invention, showing a portion of an archwire that is inserted in an archwire slot of the appliance.
Figure 2:
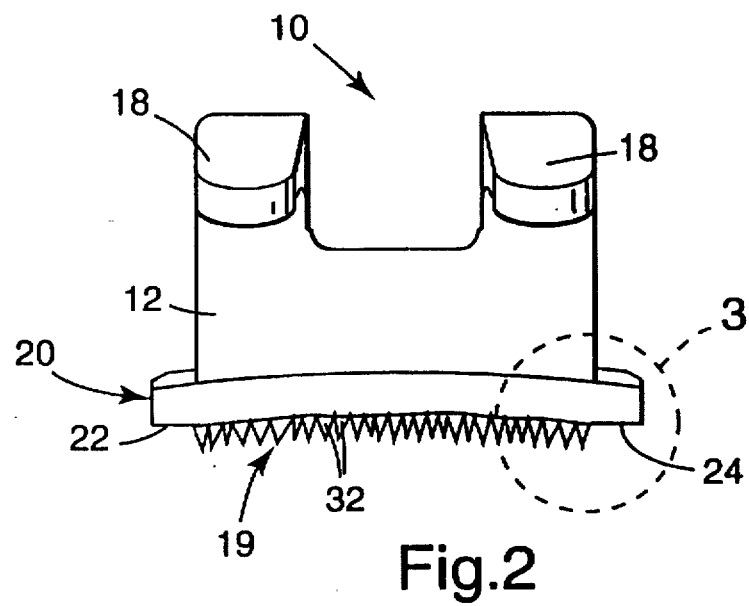
FIG. 2 is a view looking toward a gingival side of the appliance alone that is shown in FIG. 1.

An orthodontic appliance constructed in accordance with one embodiment of the present invention is designated broadly by the numeral 10 in FIGS. 1–4. The appliance 10 is shown for illustrative purposes as an orthodontic bracket having a central body 12 with wall sections that define an archwire slot 14 for receiving an archwire 16. However, the invention may be used in conjunction with other types of orthodontic appliances as well such as buccal tubes, cleats and buttons.

Four tiewings 18 are integrally connected to the body 12. A groove is located between each tiewing 18 and adjacent areas of the body 12 for presenting a channel to receive a ligature such as a section of metallic wire or an elastic O-ring. The ligature is not shown in the drawings but extends about the archwire 16 for retaining the archwire 16 in the archwire slot 14. Optionally, the body 12 may have mesial and distal sections of the type shown in U.S. Pat. Nos. 5,366,372 and 5,439,379.

The appliance 10 also includes bonding structure for directly bonding the appliance 10 to a tooth surface. The bonding structure 19 includes a base 20 that is integrally connected to the body 12. In the embodiment shown in FIGS. 1–4, the base 20 extends in a reference plane (or "plane of contour") that has a concave configuration adapted to match the convex, compound contour of the tooth for which the appliance 10 is intended. However, for some appliances, such as relatively small appliances, the reference plane or "plane of contour" may be flat or essentially flat. Preferably, the base 20 is imperforate (i.e., lacks openings that extend completely through the base 20 in a labial-lingual direction).

Figure 4:
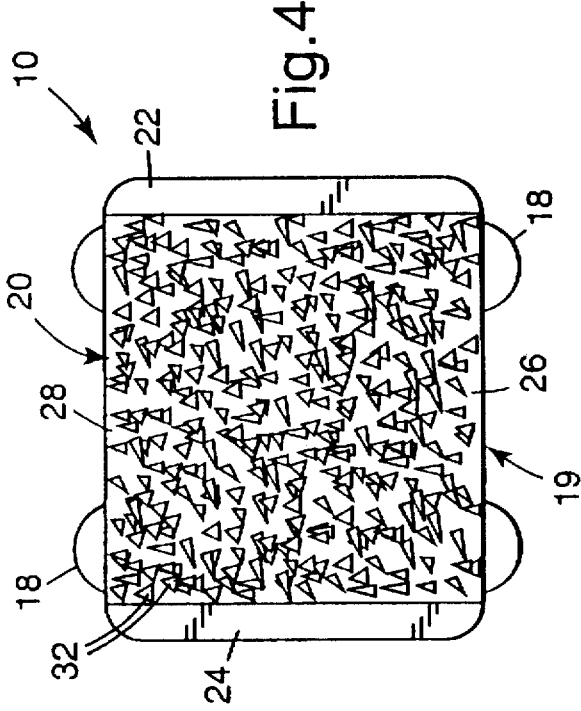
FIG. 4 is a rear view looking toward a base of the appliance shown in FIGS. 1–3.

Referring now to FIG. 4, the base 20 includes a mesial edge portion 22, a distal edge portion 24, a gingival edge portion 26 and an occlusal edge portion 28. As used herein, the term "mesial edge portion" such as portion 22 means an edge portion that extends along the entire mesial edge of the base 20, the "distal edge portion" such as portion 24 means an edge portion that extends along the entire distal edge of the base 20, the "gingival edge portion" such as portion 26 means an edge portion that extends along the entire gingival edge of the base 20 and the "occlusal edge portion" such as portion 28 means an edge portion that extends along the entire occlusal edge of the base 20. Moreover, each portion 22, 24, 26, 28 has an equal area when taken along the aforementioned plane of contour. (As such, the width of, for example, the portion 22 is not equal to the width of the portion 26 since the length of the portion 22 is unequal to the length of the portion 26.)

The bonding structure 19 includes a first means for bonding the mesial edge portion 22 to a tooth (such as tooth 30 shown in FIG. 3) with a first bond strength value. The bonding structure 19 further includes a second means for bonding the distal edge portion 24 to the tooth 30 with a second bond strength value. The bonding structure 19 also includes a third means for bonding the gingival edge portion 26 to the tooth 30 with a third bond strength value and a fourth means for bonding the occlusal edge portion 28 to the tooth 30 with a fourth bond strength value. As used herein, the "bond strength value" means the force per unit area required to detach the designated portion of the appliance from a tooth surface, wherein the area is taken along the plane of contour.

In the embodiment shown in FIGS. 1–4, the bonding structure 19 comprises a number of particles 32 that are fixed to the tooth-facing surface of the base 20. The third means and the fourth means mentioned above comprise the particles 32 that are directly connected to the gingival edge portion 26 and the occlusal edge portion 28 respectively. As shown, a substantial number of particles 32 are connected to the edge portions 26, 28. The first means and the second means mentioned above comprise a relatively smaller number of such particles 32, and preferably comprise a substantial lack of such particles 32 that are directly connected to the mesial edge portion 22 and the distal edge portion 24.

Figure 3:
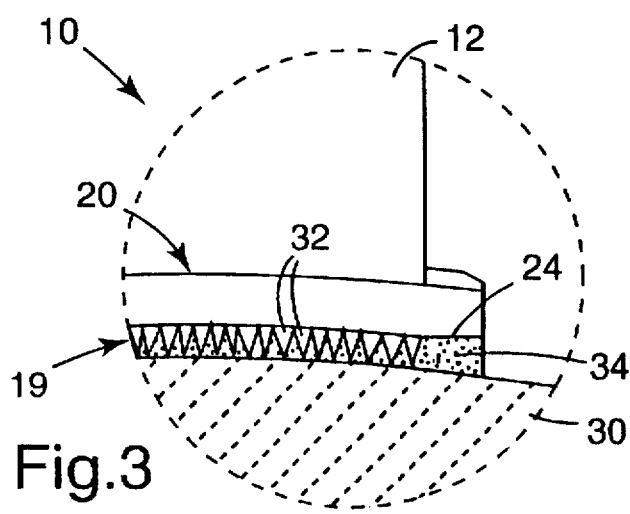
FIG. 3 is an enlarged view of a portion of the appliance shown in FIG. 2, also illustrating a quantity of adhesive for bonding the appliance to a tooth surface.

The substantial lack of particles 32 connected to the mesial and distal edge portions 22, 24 significantly lowers the strength of the adhesive bond of the appliance 10 to the tooth 30 in such portions 22, 24 in comparison to other areas of the base 20, including the gingival and occlusal edge portions 26, 28. In FIG. 3, an adhesive 34 is provided to bond the base 20 to the tooth 30, and it can be appreciated that the lack of a substantial number of particles 32 beneath the distal edge portion 24 significantly reduces the surface area of the appliance 10 in contact with the adhesive 34 in such portion. By contrast, regions of the base 20 that extend over a substantial number of the particles 32 (such as the edge portions 26, 28 as well as a central portion of the base 20) constitute regions where the appliance 10 has a significantly higher surface area in contact with the adhesive 34 and hence has relatively higher bond strength values.

The appliance 10 can be debonded from the tooth 30 when desired by the orthodontist by pivoting the appliance 10 about an occlusal-gingival axis, so that initiation of a crack in the adhesive 34 occurs in the portions 22, 24 as selected. The crack thereafter readily propagates through remaining areas of the adhesive 34. However, the particles 32 that are directly connected to the portions 26, 28 enable the appliance 10 to normally remain bonded to the tooth 30 during orthodontic treatment. For example, the particles 32 connected to the portion 26 enable the appliance 10 to withstand forces typically encountered during mastication, as might occur when the appliance 10 is contacted by a relatively hard food object.

Moreover, the appliance 10 remains bonded to the tooth 30 even when subjected to forces during orthodontic treatment that may be applied by the orthodontist through the use of bends or twists in the archwire, by wire springs or by elastic modules. For example, the archwire 16 may be intentionally twisted by the orthodontist about its long axis in order to cause the appliance 10 to tip the occlusal edge of the tooth in an outwardly direction about the arc 35 in FIG. 1. However, such torquing force as exerted by the archwire is safely resisted by the relatively high bond strength value that is present beneath the occlusal edge portion 28. The particles 32 directly connected to the portion 28 insures that the appliance 10 remains securely bonded to the tooth 30.

In some instances, the orthodontist may apply a force that establishes tensile stress beneath either of the portions 22, 24. Such stress may occur, for example, when the orthodontist desires to retract the tooth 30 for closure of a space. However, such mesial-distal forces are typically much less than forces normally encountered from an occlusal direction. For example, occlusal loads encountered during treatment may exceed 10 kg, while a mesial-distal load as may occur during retraction may be less than 500 g.

As can be appreciated, the asymmetric bonding structure 19 enables the appliance 10 to be more easily debonded from the tooth 30 when pivoted about an occlusal-gingival axis in comparison to when pivoted about a mesial-distal axis. Such bonding structure 19 is particularly an advantage for appliances 10 that are made of relatively stiff, non-ductile or brittle materials such as polycrystalline alumina. However, the invention is also useful for appliances 10 that are made of other materials such as stainless steel or plastic.

The particles 32 (shown schematically in FIG. 3) may be spherical or irregularly shaped, and may be made of the same material as the body 12 or a different material. Moreover, the particles 32 may present undercut regions, or may be connected to the base 20 in such a fashion that undercut regions are formed to establish pockets where the adhesive establishes a mechanical interlock with the base once the adhesive has hardened.

As an example, the body 12 and the base 20 may be integrally made of a polycrystalline alumina, and the particles 32 may be irregularly-shaped granules of polycrystalline alumina. Various methods for affixing ceramic particles to ceramic bodies are described in U.S. Pat. No. 5,108,285, incorporated by reference herein. The particles 32 may be affixed to the base 20 by embedding the particles 32 in a glass frit that is connected to the base 20. Alternatively, the particles 32 may be affixed to the base 20 by other means such as by diffusion bonding.

The particles 32 may be applied to the base 20 of a number of appliances 10 by loading the appliances 10 in a tray such that the base of each appliance 10 faces in an upwardly direction. The tray has grooves or other structure to hold the appliances 10 in a precise location relative to each other. Next, a sheet metal mask is placed over the appliances 10. The mask has a series of openings that are arranged to fall over preselected areas of the base 20 of each appliance 10. The particles are then directed toward the unmasked portions of each appliance base 20 and fixed in place.

If the body 12 and the base 20 are made of a metallic material, the particles 32 may be connected to the base 20 by any one of a number of various methods, such as adhesives, ion bombardment, flame-spraying, diffusion bonding or the like. Suitable methods for affixing particles to metal brackets are described in U.S. Pat. Nos. 4,752,221, 4,460,336 and 4,626,209, incorporated by reference herein.

Figure 5:
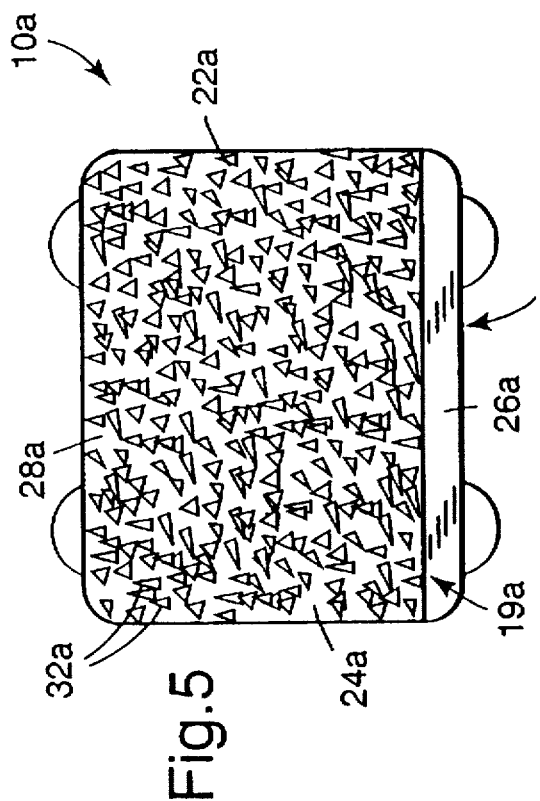
FIG. 5 is a view somewhat similar to FIG. 4 but according to another embodiment of the invention.

A second embodiment of the invention is shown in FIG. 5, wherein an appliance 10a has a body, archwire slot and tiewings similar to the body 12, the archwire slot 14 and the tiewings 18 described above. Moreover, the appliance 10a has a bonding structure 19a with a base 20a that is the same as the base 20 described above. The base 20a includes a mesial edge portion 22a, a distal edge portion 24a, a gingival edge portion 26a and an occlusal edge portion 28a that are similar to the portions 22, 24, 26, 28 respectively described above.

However, the bonding structure 19a in this instance includes particles 32a that are directly connected to the portions 22a, 24a and 28a. The portion 26a lacks direct connection to a substantial number of such particles 32a, and preferably lacks direct connection to any of such particles 32a. The particles 32a and the base 20a, as well as remaining elements of the appliance 10a, may be made of materials similar or identical to the materials set out above.

The lack of a substantial number of particles 32a connected to the gingival edge portion 26a enables the appliance 10a to be readily removed by tipping the appliance 10a in a direction such that a crack is first initiated in the adhesive located beneath the gingival edge portion 26a. However, the substantial number of particles 32a that are connected to the occlusal edge portion 28a enable the appliance 10a to be securely retained on the tooth during the ordinary course of orthodontic treatment. Although not shown, as another option the number of particles 32a, if any, directly connected to all three of the edge portions 22a, 24a, 26a may be appreciably less than the number of particles directly connected to the occlusal edge portion 28a.

Another embodiment of the invention is depicted in FIG. 6, wherein an appliance 10b has bonding structure 19b that includes a base 20b. The base 20b has a mesial edge portion 22b, a distal edge portion 24b, a gingival edge portion 26b and an occlusal edge portion 28b that are identical to the portions 22, 24, 26, 28 respectively described above.

The bonding structure 19b, however, includes a series of projections 36b that are connected to the base 20b and extend outwardly in a direction away from the body of the appliance 10b. The projections 36b optionally have a stem and a head larger than the stem, such as a peened-over, mushroom-shaped head to establish a mechanical interlock with the adhesive once hardened. Although the projections 36b depicted in FIG. 6 have a square cross-sectional configuration, it should be understood in this regard that projections of other shapes may also be used, such as cylindrical or rectangular-shaped projections. As other alternatives, the projections 36b could be regular or irregular-shaped particles such as the particles 32, 32a described above.

Each of the projections 36b has a total external surface area. The total surface area of all of the projections 36 that are directly connected to either of the portions 22b, 24b is less than the total surface area of any projections 36b that are directly connected to either of the edge portions 26b, 28b. As a consequence, the bond strength of the appliance 10b to the tooth in areas beneath the portions 26b, 28b is greater than the bond strengths in areas beneath the edge portions 22b, 24b.

In the embodiment shown in FIG. 6, the number of projections 36b directly connected to the mesial edge portion 22b and the distal edge portion 24b is less than the number of projections 36b directly connected to the gingival edge portion 26b and the occlusal edge portion 28b. Stated somewhat differently, the projections 36b connected to each of the portions 26b, 28b are spaced apart from each other a certain average distance that is less than the average distance of spacing of the projections 36b connected to each of the portions 22b, 24b. Since in this case all of the projections 36b have the same external surface area, the bond strength value is less in areas beneath the portions 22b, 24b than in areas beneath the portions 26b, 28b.

Another aspect of the invention is illustrated in FIG. 7, wherein an appliance 10c has a body, archwire slot and tiewings somewhat similar to the body 12, the archwire slot 14 and the tiewings 18 described above. A bonding structure 19c of the appliance 10c includes a base 20c. The base 20c has a mesial edge portion 22c, a distal edge portion 24c, a gingival edge portion 26c and an occlusal edge portion 28c that are similar to the portions 22, 24, 26 and 28 respectively mentioned above.

The bonding structure 19c includes a mesh pad 38c that resembles a miniature screen made of a number of interwoven, fine wires. The mesh pad 38c includes a mesial edge 40c, a distal edge 42c, a gingival edge 44c and an occlusal edge 46c.

Optionally, the body and base 20c of the appliance 10c are made of metal such as stainless steel, and the mesh pad 38c is also made of stainless steel. The mesh pad 38c is affixed to the base 20c by a welding or brazing operation. Examples of suitable mesh pads include "DYNABOND" brand bonding bases from 3M Unitek Corporation.

As shown in FIG. 7, the mesial edge 40c of the mesh pad 38c is spaced a certain distance that is greater than zero from a mesial edge 41c of the base 20c. Similarly, the distal edge 42c of the mesh pad 38c is spaced a certain distance that is greater than zero from a distal edge 43c of the base 20c. On the other hand, the gingival edge 44c and the occlusal edge 46c are coextensive with a gingival edge 45c and an occlusal edge 47c respectively of the base 20c (i.e., the edges 44c, 45c lie in a common reference plane that is perpendicular to the plane of contour of the base 20c, and the edges 46c, 47c also lie in a common reference plane that is perpendicular to the plane of contour of the base 20c). Stated somewhat differently, the edge 44c is spaced a zero distance from the edge 45c and the edge 46c is spaced a zero distance from the edge 47c when considered in directions extending along the plane of contour of the base 20c.

As a result, the bond strength values of various regions of the appliance 10c to a tooth is less in areas beneath the mesial and distal edge portions 22c, 24c than the areas beneath the gingival and occlusal edge portions 26c, 28c. The appliance 10c can be readily detached from the tooth by tipping the appliance 10c about an occlusal-gingival axis. Yet, the appliance 10c remains affixed to the tooth when desired and is able to safely withstand typically occlusal stresses as may be encountered during treatment.

Figure 8:
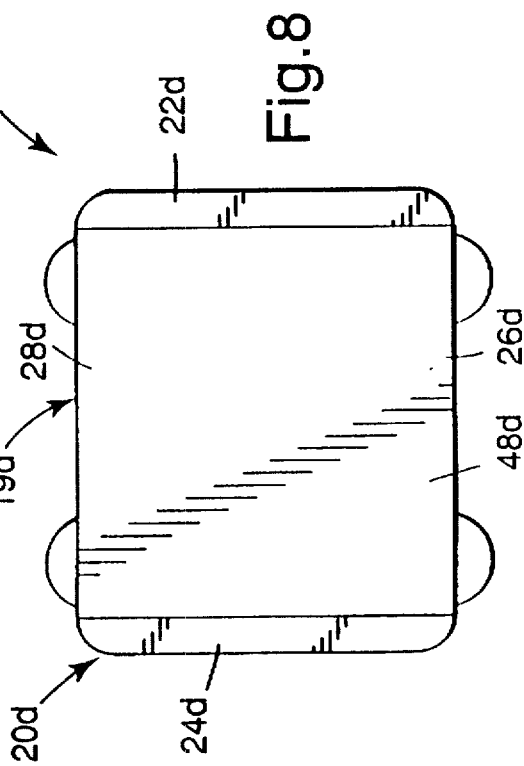
FIG. 8 is a view somewhat similar to FIG. 4 but according to another embodiment of the invention.

An orthodontic appliance 10d according to another embodiment of the invention is illustrated in FIG. 8, and includes a body, an archwire slot and tiewings that are similar to the body 12, the archwire slot 14 and the tiewings 18 respectively mentioned above. A bonding structure 19d of the appliance 10d includes a base 20d having a mesial edge portion 22d, a distal edge portion 24d, a gingival edge portion 26d and an occlusal edge portion 28d.

The bonding structure 19d also includes a material (designated by the numeral 48d in FIG. 8) for enhancing the bond strength of an orthodontic adhesive to the base 20d. For example, the material 48d may be a silane coupling agent such as gamma-methacryloxypropyl trimethoxysilane when the base 20d is made of a ceramic material such as monocrystalline or polycrystalline alumina. Other suitable materials are described in U.S. Pat. Nos. 4,948,366 and 4,673,354 which are expressly incorporated by reference herein.

The material 48d is coated onto the base 20d. The material 48d covers a larger percentage of the area of the edge portions 26d, 28d than the percent coverage of the edge portions 22d, 24d. Preferably, and as shown, the material 48d may be completely lacking along the edge portions 22d, 24d. As a consequence, the bond strength value of the appliance 10d to a tooth in areas beneath the portions 22d, 24d is less than the bond strength values beneath the portions 26d, 28d. (For purposes herein, the area of the portions 22d, 24d, 26d, 28d is considered the area that lies in the plane of contour of the base 20d that matches the convex shape of the tooth surface.)

Alternatively, the portions 22d, 24d may be coated with a material that decreases the bond strength of an orthodontic adhesive to the base 20d. In such an instance, the material 48d may be omitted or may be used in the manner described above, as desired.

Figure 9:
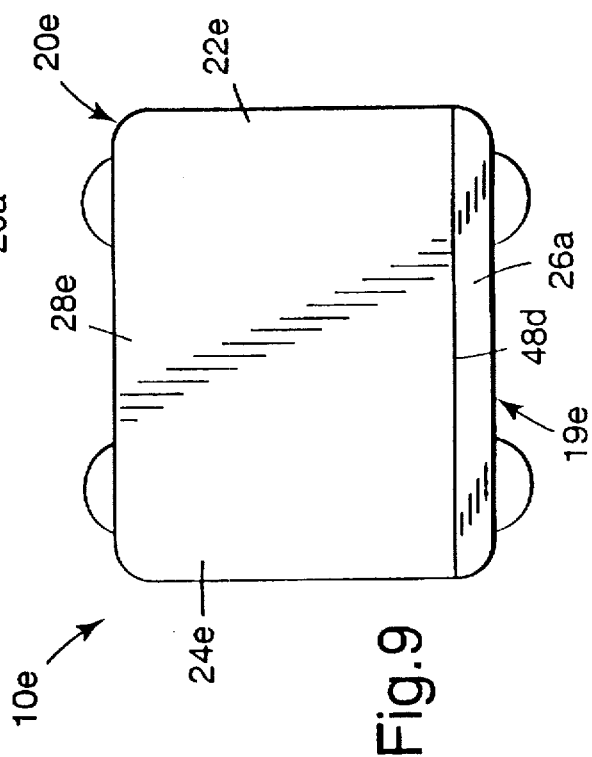
FIG. 9 is a view somewhat similar to FIG. 4 in accordance with yet another embodiment of the invention.

In FIG. 9, an orthodontic appliance 10e according to another embodiment of the invention has a body, an archwire slot and tiewings similar to the body 12, the archwire slot 14 and the tiewings 18 respectively. The appliance 10e also has bonding structure 19e that includes a base 20e having a mesial edge portion 22e, a distal edge portion 24e, a gingival edge portion 26e and an occlusal edge portion 28e.

A material 48e is coated onto the base 20e for enhancing the bond strength of an orthodontic adhesive to the base 20e. The material 48e may be identical to the material 48d described earlier. In this instance, however, since, however, the material 48e covers a larger surface area of the portions 22e, 24e and 28e than the portion 26e. As a result, the bond strength of the appliance 10e to the tooth is less in areas beneath the portion 26e than beneath the portions 22e, 24e and 28e.

FIG. 10 is an illustration of another embodiment of the invention, wherein an orthodontic appliance 10f has a body, an archwire slot and tiewings similar to the body 12, the archwire slot 14 and the tiewings 18 respectively described above. A bonding structure 19f of the appliance 10e includes a base 20f having a mesial edge portion 22f, a distal edge portion 24f, a gingival edge portion 26f and an occlusal edge portion 28f that are similar to the portions 22, 24, 26, 28 respectively described above.

The bonding structure 19f also comprises an orthodontic adhesive 50f. As can be observed in FIG. 10, the adhesive 50f has a mesial edge 41f that is spaced from a mesial edge 40f of the base 20f and a distal edge 43f that is spaced from a distal edge 42f of the base 20f when considered in directions along the plane of contour of the base 20f. However, a gingival edge 45f of the adhesive 50f is coextensive with a gingival edge 44f of the base 20f, and an occlusal edge 47f of the adhesive 50f is coextensive with an occlusal edge 46f of the base 20f.

Preferably, a second material such as an adhesive having substantially less bond strength than the adhesive 50f is applied to the base 20f beneath the mesial edge portion 22f and the distal edge portion 24f. Although not shown in the drawings, the second adhesive is useful for occupying the space between the base 20f and the surface of the tooth that might otherwise exist. As a result, areas that might otherwise trap food and the like are avoided.

The appliance 10f is preferably precoated with adhesive 50f and received in a container 52f that is depicted in FIG. 11. Suitable adhesives include "TRANSBOND" brand light-curable adhesive (from 3M Unitek Corporation) as well as the adhesives described in U.S. Pat. No. 5,354,199. The container 52f includes a lid 54f and is preferably made of a material that blocks the transmission of actinic radiation that might otherwise cure the adhesive 50f. Suitable containers 52f are described in U.S. Pat. No. 5,350,059 as well as in pending U.S. patent application Ser. No. 08/407,190 entitled "Package for Adhesive Precoated Dental Appliance."

A number of other variations of the invention are also possible. For example, a material that weakens the bond between the adhesive and the base of the appliance may be applied to the mesial, distal or gingival edge portions of the appliance base, or onto a mesh pad, particles or other structure that is applied to the base for embedment in the adhesive. As another alternative, a material that occupies openings, undercut areas and other regions of a mesh pad, roughened or scribed base or base having other types of projections or particles may be used in order to reduce the surface area of the bonding structure in certain portions or to reduce the number of undercut regions in certain portions. Examples of such material include brazing material for bases having mesh pads, and adhesives and adhesive primers for bases that have particles or projections or that are roughened or scribed.

The invention is also useful for orthodontic appliances other than brackets. For example, the appliance may be a buccal tube, a cleat, a button or other device that is directly bonded to a tooth surface. Such a device may include an open or closed slot for receiving an archwire, and the slot may have a round, rectangular or square cross-sectional configuration. The appliance may have tiewings or other structure (such as movable walls) to secure the archwire in the slot.

Those skilled in the art may recognize a number of other variations, modifications and additions that are possible without departing from the spirit of the invention. Consequently, the invention should not be deemed limited by the presently preferred embodiments that are described in detail above, but only by a fair scope of the claims that follow along with their equivalents.

We claim:

1. An orthodontic appliance comprising:

a non-plastic body having wall sections defining a slot for receiving an archwire; and bonding structure connected to said body for bonding said body to a tooth, said bonding structure including an imperforate base extending in a reference plane that matches the contour of the tooth and having a mesial edge, a distal edge, a gingival edge and an occlusal edge, said base also having a mesial edge portion, a distal edge portion, a gingival edge portion and an occlusal edge portion, said mesial edge portion, said distal edge portion, said gingival edge portion and said occlusal edge portion extending along the entire extent of said mesial edge, said distal edge, said gingival edge and said occlusal edge respectively, each of said mesial edge portion, said distal edge portion, said gingival edge portion and said occlusal edge portion having equal areas extending along said reference plane and being devoid of grooves extending inwardly from said reference plane toward said body, wherein said bonding structure includes first means for bonding said mesial edge portion to the tooth with a first bond strength value, second means for bonding said distal edge portion to the tooth with a second bond strength value, third means for bonding said gingival edge portion to the tooth with a third bond strength value and fourth means for bonding said occlusal edge portion to the tooth with a fourth bond strength value, and wherein at least one of said first bond strength value, said second bond strength value and said third bond strength value is less than said fourth bond strength value.

2. The orthodontic appliance of claim 1, wherein said first means, said second means, said third means and said fourth means each include a certain number of particles affixed to said base per unit area, and wherein said number of particles per unit area of said fourth means is greater than at least one of said certain number of particles per unit area of said first means, said second means and said third means.

3. The orthodontic appliance of claim 2, wherein said particles, said body and said base are made of a ceramic material.

4. The orthodontic appliance of claim 1, wherein said first bond strength value is approximately equal to said second bond strength value, and wherein said third bond strength value is approximately equal to said fourth bond strength value.

5. The orthodontic appliance of claim 1, wherein said third means and said fourth means include undercut areas.

6. The orthodontic appliance of claim 1, wherein said third means and said fourth means include projections connected to said base and extending outwardly from said base.

7. The orthodontic appliance of claim 1, wherein said third means and said fourth means includes a material extending over said base.

8. The orthodontic appliance of claim 1, wherein said bonding structure includes a mesh pad, and wherein said third means and said fourth means comprise portions of said mesh pad adjacent said gingival edge portion and said occlusal edge portion respectively.

9. An orthodontic appliance comprising:

a non-plastic body having wall sections defining a slot for receiving an archwire; and bonding structure connected to said body for bonding said body to a tooth, said bonding structure including a base extending in a reference plane that matches the contour of the tooth and having a mesial edge, a distal edge, a gingival edge and an occlusal edge, said base also having a mesial edge portion, a distal edge portion, a gingival edge portion and an occlusal edge portion, said mesial edge portion, said distal edge portion, said gingival edge portion and said occlusal edge portion extending along the entire extent of said mesial edge, said distal edge, said gingival edge and said occlusal edge respectively, each of said mesial edge portion, said distal edge portion, said gingival edge portion and said occlusal edge portion having equal areas extending along said reference plane and being devoid of grooves extending inwardly from said reference plane toward said body, wherein said bonding structure includes projections connected to said base and extending outwardly away from said base, wherein each of said projections has a certain surface area, and wherein the total surface area of any projections connected to one of said mesial edge portion, said distal edge portion and said gingival edge portion is less than the total surface area of any projections connected to said occlusal edge portion.

10. The orthodontic appliance of claim 9, wherein at least some of said projections include a stem and a head larger than said stem and presenting an undercut region.

11. The orthodontic appliance of claim 9, wherein said mesial edge portion and said distal edge portion lack any of said projections.

12. The orthodontic appliance of claim 9, wherein each of said mesial edge portion and said distal edge portion include projections spaced apart from each other a certain average distance, and wherein said gingival edge portion and said occlusal edge portion each include projections spaced apart from each other an average distance that is less than said certain distance.

13. An orthodontic appliance comprising:

a body having wall sections defining a slot for receiving an archwire; and bonding structure connected to said body for bonding said body to a tooth, said bonding structure including a base extending in a common reference plane that matches the contour of the tooth and having a mesial edge, a distal edge, a gingival edge and an occlusal edge, said base also having a mesial edge portion, a distal edge portion, a gingival edge portion and an occlusal edge portion, said mesial edge portion, said distal edge portion, said gingival edge portion and said occlusal edge portion extending along the entire extent of said mesial edge, said distal edge, said gingival edge and said occlusal edge respectively, each of said mesial edge portion, said distal edge portion, said gingival edge portion and said occlusal edge portion having equal areas lying in said reference plane, wherein said bonding structure includes a number of particles connected to said base along said reference plane, and wherein a greater quantity of said particles are connected to said occlusal edge portion than are connected to at least one of said mesial edge portion, said distal edge portion and said gingival edge portion.

14. The orthodontic appliance of claim 13, wherein said body and said base each comprise a ceramic material.

15. The orthodontic appliance of claim 14, wherein said particles are made of a ceramic material.

16. The orthodontic appliance of claim 13, wherein said mesial edge portion and said distal edge portion lack any of said particles.

17. An orthodontic appliance comprising:

a body having wall sections defining a slot for receiving an archwire; and bonding structure connected to said body for bonding said body to a tooth, said bonding structure including a base extending in a reference plane that matches the contour of the tooth and having a mesial edge, a distal edge, a gingival edge and an occlusal edge, said base also having a mesial edge portion, a distal edge portion, a gingival edge portion and an occlusal edge portion said mesial edge portion, said distal edge portion, said gingival edge portion and said occlusal edge portion extending along the entire extent of said mesial edge, said distal edge, said gingival edge and said occlusal edge respectively, each of said mesial edge portion, said distal edge portion, said gingival edge portion and said occlusal edge portions having equal areas lying in said reference plane, wherein said bonding structure includes a material covering at least part of said base along said reference plane for enhancing the bond strength of an orthodontic adhesive to said base, and wherein said material covers a larger percentage of said area of said occlusal edge portion than covers any percentage of the area of at least one of said mesial edge portion, said distal edge portion and said gingival edge portion.

18. The orthodontic appliance of claim 17, wherein said body and said base are made of a ceramic material, and wherein said material comprises a silane coupling agent.

19. An orthodontic appliance comprising:

a body having wall sections defining a slot for receiving an archwire; and bonding structure connected to said body for bonding said body to a tooth, said bonding structure including a base and a mesh pad connected to said base, said base and said mesh pad each having a mesial edge, a distal edge, a gingival edge and an occlusal edge, said mesial edge of said mesh pad being located a first distance from said mesial edge of said base, said distal edge of said mesh pad being located a second distance from said distal edge of said base, said gingival edge of said mesh pad being located a third distance from said gingival edge of said base, said occlusal edge of said mesh pad being located a fourth distance from said occlusal edge of said base, and wherein said fourth distance is less than at least one of said first distance, said second distance and said third distance.

20. The orthodontic appliance of claim 19, wherein said first distance is approximately equal to said second distance.

21. The orthodontic appliance of claim 20, wherein said third distance is approximately equal to said fourth distance.

22. The orthodontic appliance of claim 21, wherein said third distance and said fourth distance is approximately zero.

23. An orthodontic appliance of claim 19, wherein said base is made of a metallic material, and wherein said mesh pad is made of a metallic material that is affixed to said base.

24. A packaged orthodontic article comprising:

a container; and an orthodontic appliance removably received in said container, said appliance including a body removably received in said container, said body having wall sections defining a slot for receiving an archwire, and bonding structure connected to said body for bonding said body to a tooth, said bonding structure including a base and a quantity of adhesive connected to said base, said base and said adhesive each having a mesial edge, a distal edge, a gingival edge and an occlusal edge, said mesial edge of said adhesive being located a first distance from said mesial edge of said base, said distal edge of said adhesive being located a second distance from said distal edge of said base, said gingival edge of said adhesive being located a third distance from said gingival edge of said base, said occlusal edge of said adhesive being located a fourth distance from said occlusal edge of said base, and wherein said fourth distance is less than at least one of said first distance, said second distance and said third distance.

25. The orthodontic appliance of claim 24, wherein said first distance is approximately equal to said second distance.

26. The orthodontic appliance of claim 25, wherein said third distance is approximately equal to said fourth distance.

27. The orthodontic appliance of claim 24, wherein said fourth distance is approximately zero.

* * * * *